(12) United States Patent
Hata et al.

(10) Patent No.: US 8,288,329 B2
(45) Date of Patent: Oct. 16, 2012

(54) HAIR-TREATMENT COMPOSITION AND HAIR-TREATMENT METHOD USING SAME

(75) Inventors: Masakatsu Hata, Aichi-ken (JP); Akihiko Arai, Aichi-ken (JP)

(73) Assignee: Hoyu Co., Ltd, Aichi-ken (JP)

( * ) Notice: Subject to any disclaimer, the term of this patent is extended or adjusted under 35 U.S.C. 154(b) by 0 days.

(21) Appl. No.: 13/376,510

(22) PCT Filed: Jun. 10, 2010

(86) PCT No.: PCT/JP2010/059873
§ 371 (c)(1),
(2), (4) Date: Dec. 6, 2011

(87) PCT Pub. No.: WO2010/143695
PCT Pub. Date: Dec. 16, 2010

(65) Prior Publication Data
US 2012/0100091 A1    Apr. 26, 2012

(30) Foreign Application Priority Data
Jun. 12, 2009    (JP) .................................. 2009-141537

(51) Int. Cl.
*A61Q 5/00* (2006.01)
(52) U.S. Cl. ..... 510/119; 510/123; 510/126; 424/70.21; 424/70.23
(58) Field of Classification Search .................. 510/119, 510/123, 126; 424/70.21, 70.23
See application file for complete search history.

(56) References Cited

U.S. PATENT DOCUMENTS

2007/0265181 A1*  11/2007  Kikuchi et al. ............... 510/125

FOREIGN PATENT DOCUMENTS

| GB | 1378955 | 2/1975 |
|---|---|---|
| JP | 2003-095876 | 4/2003 |
| JP | 2005-041844 | 2/2005 |
| JP | 2005-041845 | 2/2005 |
| JP | 2006-022085 | 1/2006 |
| JP | 2007-302736 | 11/2007 |
| JP | 2008-144057 | 6/2008 |
| JP | 2008-266184 | 11/2008 |
| JP | 47-033109 | 12/2011 |

OTHER PUBLICATIONS

STIC Search Report dated Apr. 25, 2012.*
The translation of the International Preliminary Report on Patentability mailed Aug. 24, 2010 for International Application No. PCT/JP2010/059873. Filed Jun. 10, 2010.

* cited by examiner

*Primary Examiner* — Eisa Elhilo
(74) *Attorney, Agent, or Firm* — Seager, Tufte & Wickhem LLC

(57) ABSTRACT

Provided is a hair-treatment composition containing: a first amphoteric surfactant having a structure represented by general formula (1) below; at least one type of second amphoteric surfactant selected from the group consisting of fatty acid amide propyldimethylaminoacetic acid betaines, alkyldimethylaminoacetic acid betaines, N-acylaminoethyl-N-2-hydroxyethylaminocarboxylic acid salts and N-acylaminoethyl-N-carboxymethoxyethylaminocarboxylic acid salts fatty acid amide propyldimethylaminoacetic acid betaines, alkyldimethylaminoacetic acid betaines; and an acidic amino acid. In general formula (1), $R^1$ represents an alkyl group the carbon number of which is 6 to 20; $R^2$ represents a methyl group, an ethyl group, or a hydroxyethyl group; $R^3$ represents a methyl group, an ethyl group, or a —$CH_2COOH$ group; and n is an integer from 1 to 3.

$$R^1-\underset{\underset{OH}{|}}{CH}-CH_2-\underset{\underset{R^3}{|}}{\overset{\overset{R^2}{|}}{N^+}}-(CH_2)_n-COO^- \quad (1)$$

6 Claims, No Drawings

HAIR-TREATMENT COMPOSITION AND HAIR-TREATMENT METHOD USING SAME

TECHNICAL FIELD

The present invention relates to a hair-treatment composition containing a carboxybetaine-type amphoteric surfactant, and to a hair-treatment method which uses the same.

BACKGROUND ART

Patent Document 1 discloses novel carboxybetaine-type amphoteric surfactants. When hair-treatment compositions containing such amphoteric surfactants are used on dyed keratin fibers, they exhibit a color-retaining effect, that is, a color fade suppressing effect, on the dyed keratin fibers. Examples of the amphoteric surfactants disclosed in Patent Document 1 include $C_{12-14}$ hydroxyalkyl hydroxyethyl sarcosine.

Patent Document 1: Japanese Laid-Open Patent Publication No. 2006-22085

SUMMARY OF THE INVENTION

Problems that the Invention is to Solve

A drawback of the color fade suppressing effect of the above amphoteric surfactants is that it tends to be inhibited by other amphoteric surfactants used to increase the foaming properties of the hair-treatment composition.

Accordingly, one objective of the invention is to provide a hair-treatment composition which has high foaming properties and also has a high dyed hair color fade suppressing effect. Another objective of the invention is to provide a hair-treatment method which uses such a composition.

Means for Solving the Problems

To achieve the foregoing objective and in accordance with a first aspect of the present invention, a hair-treatment composition is provided that includes:

(A) a first amphoteric surfactant having a structure represented by the following general formula (1)

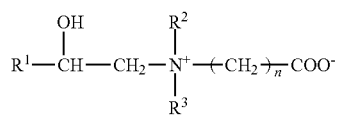

(where $R^1$ represents an alkyl group the carbon number of which is 6 to 20; $R^2$ represents a methyl group, an ethyl group, or a hydroxyethyl group; $R^3$ represents a methyl group, an ethyl group, or a —$CH_2COOH$ group; and n is an integer from 1 to 3);

(B) at least one type of second amphoteric surfactant selected from the group consisting of fatty acid amide propyldimethylaminoacetic acid betaines, alkyldimethylaminoacetic acid betaines, N-acylaminoethyl-N-2-hydroxyethylaminocarboxylic acid salts, and N-acylaminoethyl-N-carboxymethoxyethylaminocarboxylic acid salts; and (C) an acidic amino acid.

The acidic amino acid is preferably of at least one type selected from the group consisting of L-glutamic acid, L-aspartic acid, and taurine.

The second amphoteric surfactant is preferably of at least one type selected from the group consisting of cocamidopropyl betaine, lauryldimethylaminoacetic acid betaine, sodium cocoamphoacetate, sodium cocoamphopropionate, sodium cocoamphodiacetate, and sodium cocoamphodipropionate.

The hair-treatment composition according to the above first aspect of the invention is adapted for use in a post-treatment for hair after the hair is dyed with, for example, an oxidative hair dye.

In accordance with a second aspect of the present invention, a hair-treatment method is provided that includes applying the hair-treatment composition according to the above described first aspect to hair in a wet state immediately after the hair is dyed with an oxidative hair dye.

The hair-treatment method may include, following application of the hair-treatment composition to hair: washing and drying the hair; and applying the same hair-treatment composition again to the washed and dried hair.

Effects of the Invention

The invention thus provides a hair-treatment composition which has high foaming properties and has a high dyed hair color fade suppressing effect, and also provides a hair-treatment method which uses such a composition.

MODES FOR CARRYING OUT THE INVENTION

One embodiment of the invention will be described below.

A hair-treatment composition according to this embodiment contains (A) a first amphoteric surfactant having a structure of general formula (1) below. In general formula (1), $R^1$ represents an alkyl group the carbon number of which is 6 to 20; $R^2$ represents a methyl group, an ethyl group, or a hydroxyethyl group; $R^3$ represents a methyl group, an ethyl group, or a —$CH_2COOH$ group; and n is an integer from 1 to 3.

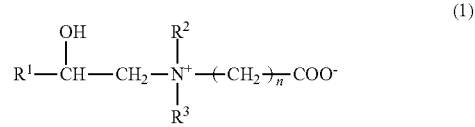

The hair-treatment composition also contains (B) at least one type of second amphoteric surfactant selected from the group consisting of fatty acid amide propyldimethylaminoacetic acid betaines, alkyldimethylaminoacetic acid betaines, N-acylaminoethyl-N-2-hydroxyethylaminocarboxylic acid salts, and N-acylaminoethyl-N-carboxymethoxyethylaminocarboxylic acid salts; and (C) an acidic amino acid.

The first amphoteric surfactant functions to suppress the color fading of dyed hair. In general formula (1), $R^2$ is preferably a hydroxyethyl group. Specific examples of the first amphoteric surfactant include amphoteric surfactants commercially available under the International Nomenclature Cosmetic Ingredient (INCI) name of $C_{12-14}$ hydroxyalkyl hydroxyethyl sarcosine.

The content of the first amphoteric surfactant in the hair-treatment composition is preferably from 0.01 to 30% by mass, more preferably from 0.05 to 20% by mass, and even more preferably from 0.1 to 10% by mass. When the content of the first amphoteric surfactant is 0.01% by mass or higher, a pronounced dyed hair color fade suppressing effect is easily obtained. However, when the content of the first amphoteric surfactant is in excess of 30% by mass, hair that has been washed and dried following treatment with the hair-treatment composition may become sticky.

The second amphoteric surfactant functions to increase the foaming properties of the hair-treatment composition. Specific examples of fatty acid amide propyldimethylaminoacetic acid betaines include coconut oil fatty acid amide propyldimethylaminoacetic acid betaine (cocamidopropylbetaine), palm oil fatty acid amide propyldimethylaminoacetic acid betaine, lauric acid amide propyldimethylaminoacetic acid betaine (lauramidopropylbetaine), and ricinoleic acid amide propyldimethylaminoacetic acid betaine. The fatty acid amide propyldimethylaminoacetic acid betaine may be contained in the form of a salt, such as a sodium salt, potassium salt, or triethanolamine salt.

Specific examples of alkyldimethylaminoacetic acid betaines include decyldimethylaminoacetic acid betaine, lauryldimethylaminoacetic acid betaine, myristyldimethylaminoacetic acid betaine, cetyldimethylaminoacetic acid betaine, stearyldimethylaminoacetic acid betaine, oleyldimethylaminoacetic acid betaine, behenyldimethylaminoacetic acid betaine, and coconut oil alkyldimethylaminoacetic acid betaine. The alkyldimethylaminoacetic acid betaine may be contained in the form of a salt, such as a sodium salt, potassium salt, or triethanolamine salt.

Specific examples of N-acylaminoethyl-N-2-hydroxyethylaminocarboxylic acid salts include sodium cocoamphoacetate (N-coconut oil fatty acid acyl-N'-carboxymethyl-N'-hydroxyethyl ethylenediamine, also known by the name of 2-alkyl-N-carboxymethyl-N-hydroxyethylimidazolinium betaine), sodium cocoamphopropionate (N-coconut oil fatty acid acyl-N'-carboxyethyl-N'-hydroxyethyl ethylenediamine), sodium lauroamphoacetate (N-lauroyl-N'-carboxymethyl-N'-hydroxyethyl ethylenediamine), sodium olive amphoacetate, sodium cocoa butter amphoacetate, sodium sesame amphoacetate, sodium sweet almond amphoacetate, stearoamphoacetic acid salts, sodium palm amphoacetate, sodium peanut amphoacetate, sodium sunflower seed amphoacetate, and sodium cotton seed amphoacetate.

Specific examples of N-acylaminoethyl-N-carboxymethoxyethylaminocarboxylic acid salts include sodium cocoamphodiacetate, sodium cocoamphodipropionate, and sodium lauroamphodiacetate.

Of these, the second amphoteric surfactant is preferably of at least one type selected from among cocamidopropyl betaine, lauryldimethylaminoacetic acid betaine, sodium cocoamphoacetate, sodium cocoamphopropionate, sodium cocoamphodiacetate, and sodium cocoamphodipropionate.

The second amphoteric surfactant content in the hair-treatment composition is preferably from 0.01 to 30% by mass, more preferably from 0.05 to 20% by mass, and even more preferably from 0.1 to 10% by mass. When the content of the second amphoteric surfactant is 0.01% by mass or higher, a pronounced hair-treatment composition foaming property increasing effect is easily obtained. However, when the content of the second amphoteric surfactant is in excess of 30% by mass, hair that has been washed and dried following treatment with the hair-treatment composition may become sticky.

An acidic amino acid is used to suppress color fading of the dyed hair and improve the foaming properties of the hair-treatment composition. Specific examples of the acidic amino acid include aspartic acid, glutamic acid, 4-carboxyglutamic acid, S-carboxymethyl cysteine, cysteic acid, taurine (aminoethylsulfonic acid), acetylglutamic acid, and pyrrolidonecarboxylic acid salts. The acetic amino acid used may be of a single type, or two or more acidic amino acids may be used in combination. When the acidic amino acid used has optical isomers, the L form, D form, or DL form may be used. The acidic amino acid may be contained in the form of a salt, such as a sodium salt, potassium salt, triethanolamine salt, or zinc salt. Of the above acidic amino acids, the use of at least one selected from among taurine, L-glutamic acid, and L-aspartic acid is preferred.

The acidic amino acid content in the hair-treatment composition is preferably from 0.001 to 5% by mass, and more preferably from 0.005 to 3% by mass. When the content of the acidic amino acid is 0.001% by mass or higher, a pronounced dyed hair color fade suppressing effect and a pronounced hair-treatment composition foaming property increasing effect is easily obtained. However, when the content of the acidic amino acid is in excess of 5% by mass, the hair tends to feel sticky following treatment with the hair-treatment composition.

The hair-treatment composition may optionally include also, for example, any of water, lower alcohols, water-soluble copolymeric compounds, oil-based ingredients, polyhydric alcohols, additional surfactants, sugars, preservatives, stabilizers, pH adjustors, plant and microbial extracts, protein hydrolyzates, crude drug extracts, vitamins, fragrances, antioxidants, ultraviolet absorbers, chelating agents, and inorganic salts.

Water and lower alcohols serve as solvents or dispersants for the various ingredients in the hair-treatment composition.

Water-soluble polymeric compounds that may be used include anionic, cationic, nonionic, or amphoteric polymeric compounds. Any such compound that is a natural compound or a synthetic compound may be used. Specific examples of cationic water-soluble polymeric compounds include poly (dimethylmethylenepiperidinium chloride) liquids, hydroxyethyl cellulose dimethyldiallylammonium chloride, polyquaternium-10, and cationized guar gum. Specific examples of nonionic water-soluble synthetic polymeric compounds include hydroxyethyl cellulose and polyethylene glycol. Specific examples of amphoteric water-soluble synthetic polymeric compounds include polyquaternium-22, polyquaternium-39, and polyquarternium-47.

Specific examples of oil-based ingredients include oils and fats, waxes, higher alcohols, hydrocarbons, higher fatty acids, alkyl glyceryl ethers, esters, and silicones.

Specific examples of oils and fats include lanolin, olive oil, camellia oil, shear nut oil, almond oil, safflower oil, sunflower oil, soybean oil, cottonseed oil, sesame oil, corn oil, rapeseed oil, rice bran oil, rice germ oil, grapeseed oil, avocado oil, macadamia nut oil, castor oil, coconut oil, and evening primrose oil.

Specific examples of waxes include beeswax, candelilla wax, carnauba wax, jojoba wax, and lanoline.

Specific examples of higher alcohols include cetyl alcohol (cetanol), 2-hexyldecanol, stearyl alcohol, isostearyl alcohol, cetostearyl alcohol, oleyl alcohol, arachyl alcohol, behenyl alcohol, 2-octyldodecanol, lauryl alcohol, myristyl alcohol, decyltetradecanol, and lanolin alcohol.

Specific examples of hydrocarbons include paraffins, olefin oligomers, polyisobutene, hydrogenated polyisobutene, mineral oils, squalane, polybutene, polyethylene, microcrystalline wax, and vaseline.

Specific examples of higher fatty acids include lauric acid, myristic acid, palmitic acid, stearic acid, behenic acid, isostearic acid, 12-hydroxystearic acid, oleic acid, and lanoline fatty acids.

Specific examples of alkyl glyceryl ethers include batyl alcohol, chimyl alcohol, selachyl alcohol, and isostearyl glyceryl ether.

Specific examples of esters include diisopropyl adipate, isopropyl myristate, cetyl octanoate, isononyl isononanoate, octyldodecyl myristate, isopropyl palmitate, stearyl stearate, myristyl myristate, isotridecyl myristate, 2-ethylhexyl palmitate, octyldodecyl ricinoleate, cholesteryl/lanosteryl fatty acids the carbon number of which is 10 to 30, cetyl lactate, lanoline acetate, ethylene glycol di-2-ethylhexanoate, fatty acid esters of pentaerythritol, fatty acid esters of dipentaerythritol, cetyl caprate, glyceryl tricaprate, diisostearyl malate, dioctyl succinate, and cetyl 2-ethylhexanoate.

Specific examples of silicones include dimethylpolysiloxane (dimethicone), methylphenylpolysiloxane, decamethylcyclopentasiloxane, dodecamethylcyclohexasiloxane, terminal hydroxy-modified dimethylpolysiloxane, highly polymerized silicones having an average degree of polymerization of from 650 to 10,000, polyether-modified silicones, amino-modified silicones, betaine-modified silicones, alkyl-modified silicones, alkoxy-modified silicones, carboxy-modified silicones, and fluorine-modified silicones.

Specific examples of polyhydric alcohols include glycols and glycerols. Specific examples of glycols include ethylene glycol, diethylene glycol, triethylene glycol, polyethylene glycol, propylene glycol, dipropylene glycol, isoprene glycol, and 1,3-butylene glycol. Specific examples of glycerols include glycerol, diglycerol, and polyglycerol.

The surfactants used may be anionic, cationic, or nonionic. Amphoteric surfactants other than the above first and second amphoteric surfactants may also be used.

Specific examples of anionic surfactants include alkyl ether sulfates, alkyl sulfates, alkenyl ether sulfates, alkenyl sulfates, olefin sulfonates, alkane sulfonates, saturated or unsaturated fatty acid salts, alkyl or alkenyl ether carboxylic acid salts, a-sulfone fatty acid salts, N-acylamino acid surfactants such as triethanolamine cocoyl glutamate (TEA cocoyl glutamate), phosphate mono- or diester surfactants, and sulfosuccinic acid esters. The counterions of the anionic groups on these surfactants are exemplified by sodium ions, potassium ions and triethanolamine ions. For example, sodium lauryl sulfate, which is a salt of an alkyl sulfuric acid, may be used.

Specific examples of cationic surfactants include lauryltrimethylammonium chloride, cetyltrimethylammonium chloride (cetrimonium chloride), stearyltrimethylammonium chloride (stearyltrimonium chloride), behenyltrimethylammonium chloride (behentrimonium chloride), distearyldimethylammonium chloride, alkyltrimethylammonium chloride, distearyldimethylammonium chloride (distearyldimonium chloride), cetyltrimethylammonium bromide, stearyltrimethylammonium bromide, lanolin fatty acid aminopropylethyldimethylammonium ethyl sulfate, stearyltrimethylammonium saccharin, cetyltrimethylammonium saccharin, methacryloyloxyethyltrimethylammonium chloride, behenyltrimethylammonium methyl sulfate, and quaternium-91.

Specific examples of amphoteric surfactants other than the first and second amphoteric surfactants include sulfobetaine-type amphoteric surfactants.

Specific examples of nonionic surfactants include ether-type nonionic surfactants and ester-type nonionic surfactants.

Specific examples of ether-type nonionic surfactants include polyoxyethylene (hereinafter referred to as POE) cetyl ether (ceteth), POE stearyl ether (steareth), POE behenyl ether, POE oleyl ether (oleth), POE lauryl ether (laureth), POE octyl dodecyl ether, POE hexyl decyl ether, POE isostearyl ether, POE nonyl phenyl ether, POE octyl phenyl ether, POE cetyl stearyl diether, and POE lauric acid monoethanolamide.

Specific examples of ester-type nonionic surfactants include POE sorbitan monooleate, POE sorbitan monostearate, POE sorbitan monopalmitate, POE sorbitan monolaurate, POE sorbitan trioleate, POE glyceryl monostearate, POE glyceryl monomyristate, POE sorbitol tetraoleate, POE sorbitol hexastearate, POE sorbitol monolaurate, POE sorbitol beeswax, polyethylene glycol monooleate, polyethylene glycol monostearate, polyethylene glycol monolaurate, polyethylene glycol distearate, lipophilic glyceryl monooleate, lipophilic glyceryl monostearate, self-emulsifying glyceryl monostearate, sorbitan monooleate, sorbitan sesquioleate, sorbitan trioleate, sorbitan monostearate, sorbitan monopalmitate, sorbitan monolaurate, sucrose fatty acid esters, decaglyceryl monolaurate (polyglyceryl laurate-10), decaglyceryl monostearate, decaglyceryl monooleate, and decaglyceryl monomyristate.

Specific examples of sugars include sorbitol, maltose, and glycosyl trehalose.

Specific examples of preservatives include sodium benzoate, methyl paraben, and phenoxyethanol.

Specific examples of stabilizers include phenacetin, 8-hydroxyquinoline, acetanilide, sodium pyrophosphate, barbituric acid, uric acid, and tannic acid.

Specific examples of pH adjustors include lactic acid, levulinic acid, glycolic acid, tartaric acid, malic acid, succinic acid, citric acid, 2-amino-2-methyl-1-propanol (AMP), and triethanolamine (TEA).

Specific examples of plant and microbial extracts include hydrolyzed yeast extracts having a moisture-retaining effect.

Specific examples of protein hydrolyzates include (dihydroxymethylsilylpropoxy)hydroxypropyl-hydrolyzed collagen and hydroxypropyltrimonium-hydrolyzed wheat protein.

Specific examples of antioxidants include ascorbic acid and sulfites.

Specific examples of chelating agents include ethylenediaminetetraacetic acid (EDTA), diethylenetriaminepentaacetic acid and salts thereof, and hydroxyethanediphosphonic acid (HEDP, etidronic acid), and salts thereof.

Specific examples of inorganic salts include sodium chloride and sodium carbonate.

The hair-treatment composition may additionally include at least one type of ingredient selected from among those listed in "Japanese Standards of Quasi-Drug Ingredients" (published June 2006 by Yakuji Nippo, Ltd.).

Examples of the form of the hair-treatment composition include, but are not limited to, aqueous solutions, dispersions, emulsions, gels, foams, and creams.

The hair-treatment composition is used to suppress color fading in hair which has been dyed using an oxidative hair dye.

The oxidative hair dye is composed of a first agent containing an oxidation dye and an alkali agent, and a second agent containing an oxidizing agent. Oxidative hair dyes are prepared by mixing the first agent and the second agent at the time of use.

The oxidation dye contained in the first agent of the oxidative hair dye undergoes color development due to oxidative polymerization by the oxidizing agent contained in the second agent of the oxidative hair dye, and contains at least a dye intermediate. The oxidation dye may include also a coupler in addition to the dye intermediate.

Specific examples of the dye intermediate include phenylenediamines (exclusive of m-phenylenediamine), aminophenols (exclusive of m-aminophenol, 2,4-diaminophenol and p-methylaminophenol), toluylenediamines (exclusive of toluene-3,4-diamine and toluene-2,4-diamine), diphenylamines, diaminophenylamines, N-phenylphenylenediamines, diaminopyridines (exclusive of 2,6-diaminopyridine), and salts thereof, such as chlorides, sulfates, and acetates. The dye intermediates used may be of a single type, or two or more dye intermediates may be used in combination.

The coupler induces color development by coupling with the dye intermediate. Specific examples of couplers include resorcinol, pyrogallol, catechol, m-aminophenol, m-phenylenediamine, 2,4-diaminophenol, 1,2,4-benzenetriol, toluene-3,4-diamine, toluene-2,4-diamine, hydroquinone, α-naphthol, 2,6-diaminopyridine, 1,5-dihydroxynaphthalene, 5-amino-o-cresol, p-methylaminophenol, 2,4-diaminophenoxyethanol, gallic acid, tannic acid, ethyl gallate, methyl gallate, propyl gallate, nutgall, 5-(2-hydroxyethylamino)-2-methylphenol, and salts thereof. The coupler used may be of a single type, or two or more couplers may be used in combination.

An oxidative dye containing a dye intermediate and a coupler is preferably used on account of the ability to change the color tone of the hair as desired.

The content of dye intermediate in the oxidative hair dye is preferably from 0.01 to 10% by mass, and more preferably from 0.1 to 5% by mass. When the content of the dye intermediate is below 0.01% by mass, it may not be possible to sufficiently dye the hair. A dye intermediate content in excess of 10% by mass is not cost-effective.

The coupler content in the oxidative hair dye is preferably from 0.01 to 5% by mass, and more preferably from 0.1 to 3% by mass. When the content of the coupler content is below 0.01% by mass, it may not be possible to sufficiently dye the hair. A coupler content in excess of 5% by mass is not cost-effective.

The first agent of the oxidative hair dye may additionally include an oxidation dye listed in "Japanese Standards of Quasi-Drug Ingredients" (published June 2006 by Yakuji Nippo, Ltd.), or may additionally include a direct dye.

The alkali agent contained in the first agent of the oxidative hair dye promotes the action of the oxidizing agent contained in the second agent of the oxidative hair dye and also, by causing the hair to swell and improving penetration of the dye into the hair, improves the dyeability of the hair by the oxidative hair dye. Specific examples of the alkali agent used include ammonia, alkanolamines, organic amines, inorganic alkalis, basic amino acids, and salts thereof. Specific examples of organic amines include 2-amino-2-methyl-1,3-propanediol and guanidine. Specific examples of inorganic alkalis include sodium hydroxide, potassium hydroxide, sodium carbonate, and potassium carbonate. Specific examples of basic amino acids include arginine and lysine. Specific examples of salts include ammonium salts. The alkali agent used may be of only one type, or two or more alkali agents may be used in combination.

The alkali agent is preferably contained in the first agent in an amount such as to render the pH of the first agent of the oxidative hair dye in a range of from 8 to 12. In the case where the pH of the first agent pH is below 8, when the first agent and second agent are mixed, the action of the oxidizing agent, especially hydrogen peroxide, contained in the second agent may not be sufficiently promoted. At a first agent pH above 12, the hair tends to become damaged when the oxidative hair dye is applied thereto.

The content of the alkali agent in the first agent of the oxidative hair dye is preferably from 0.1 to 12% by mass, more preferably from 0.2 to 11% by mass, even more preferably from 0.6 to 10% by mass, and most preferably from 0.6 to 9% by mass. When the content of the alkali agent content is below 0.1% by mass, it may not be possible to uniformly dye the hair with the oxidative hair dye. When the content of the alkali agent is in excess of 12% by mass, the hair may not have a good tactile feel following treatment with the oxidative hair dye.

The first agent of the oxidative hair dye additionally contains a predetermined amount of water, and is prepared as an emulsion, a solution, or a dispersion. The water content in the first agent is preferably from 50 to 95% by mass, and more preferably from 70 to 90% by mass. When the content of water is below 50% by mass, it may be difficult to prepare the first agent as an emulsion, a solution, or a dispersion. When the content of water is in excess of 95% by mass, it may be difficult to ensure the uniformity and stability of the first agent.

Where necessary, the first agent of the oxidative hair dye may further include at least one type of additive selected from among, for example, oil-based ingredients, surfactants, water-soluble polymeric compounds, polyhydric alcohols, sugars, preservatives, chelating agents, stabilizers, pH adjustors, plant and microbial extracts, crude drug extracts, vitamins, fragrances, and ultraviolet absorbers. Some of the details concerning these ingredients duplicate the description given of the hair-treatment composition and thus are omitted here.

The form of the first agent of the oxidative hair dye is not particularly limited, and may be, for example, an aqueous solution, a dispersion, an emulsion, a gel, a foam, or a cream.

The oxidizing agent contained in the second agent of the oxidative hair dye induces color development by oxidatively polymerizing the oxidation dye contained in the first agent. Examples of the oxidizing agent used include hydrogen peroxide, urea peroxide, melamine peroxide, sodium percarbonate, potassium percarbonate, sodium perborate, potassium perborate, sodium peroxide, potassium peroxide, magnesium peroxide, barium peroxide, calcium peroxide, strontium peroxide, the hydrogen peroxide adducts of sulfates, the hydrogen peroxide adducts of phosphates, and the hydrogen peroxide adducts of pyrophosphates. The oxidizing agent used may be of only one type, or two or more oxidizing agents may be used in combination. Hydrogen peroxide is preferred as the oxidizing agent because it has an excellent ability to decolorize the melanin contained in hair.

The content of the oxidizing agent in the second agent of the oxidative hair dye is preferably from 0.1 to 10.0% by mass, and more preferably from 0.5 to 8.0% by mass. When the content of the oxidizing agent is below 0.1% by mass, it may be difficult to sufficiently oxidatively polymerize the oxidation dye contained in the first agent. When the content of the oxidizing agent is in excess of 10.0% by mass, the hair tends to be easily damaged by the oxidative hair dye.

Where necessary, the second agent of the oxidative hair dye may further include at least one type of additive selected from among water, oil-based ingredients, surfactants, water-soluble polymeric compounds, polyhydric alcohols, sugars, preservatives, chelating agents, stabilizers, pH adjustors, plant and microbial extracts, crude drug extracts, vitamins, fragrances, and ultraviolet absorbers. Some of the details concerning these ingredients duplicate the description given of the hair-treatment composition and thus are omitted here. The second agent may additionally include at least one type of ingredient selected from among those listed in "Japanese Standards of Quasi-Drug Ingredients" (published June 2006 by Yakuji Nippo, Ltd.).

The form of the second agent of the oxidative hair dye is not subject to any particular limitation, and may be, for example, an aqueous solution, a dispersion, an emulsion, a gel, a foam, or a cream.

The oxidative hair dye is applied to the hair and thereby used to color the hair. Oxidative hair dye that has been applied to the hair is rinsed off with, for example, warm water.

The above described hair-treatment composition of the embodiment may be applied to hair that has been dyed using an oxidative hair dye for the purpose of suppressing color fading in the hair. In other words, the hair-treatment composition may be used in the post-treatment of hair that has been dyed using an oxidative hair dye. The hair-treatment composition is preferably applied to hair in a wet state immediately after the hair is dyed with an oxidative hair dye; that is, to hair which is not dried and remains in a wet state after having been dyed with an oxidative hair dye. This enables the color tone of the hair immediately after dyeing to be easily maintained.

Hair to which the hair-treatment composition has been applied following dyeing with an oxidative hair dye can, after being washed and dried, have the same hair-treatment composition again applied thereto. In such a case, color fading of the dyed hair can be even further suppressed. After being dyed, the hair may be dried with a hair dryer or may be air-dried.

The embodiment described above in detail achieves the following advantages.

Since the hair-treatment composition of this embodiment contains an acidic amino acid in addition to the first and second amphoteric surfactants, it has high foaming properties and also strongly suppresses color fading in dyed hair. The reason that color fading in dyed hair is strongly suppressed by the hair-treatment composition is presumably because the first amphoteric surfactant and the acidic amino acid contained in the hair-treatment composition protect the surface of the hair, helping to prevent the release of dye from the hair.

When the acidic amino acid contained in the hair-treatment composition is one or more selected from among L-glutamic acid, L-aspartic acid, and taurine, further improvements are achieved in the foaming properties of the hair-treatment composition and in the color fade suppressing effects by the hair-treatment composition on dyed hair.

Hair which has been dyed with an oxidizing hair dye generally undergoes greater damage than hair which has been dyed with an acidic hair color (hair manicure). In the case of hair which is strongly damaged in this way, unless the hair-treatment composition has high foaming properties, it does not conform well to the hair, making the composition difficult to apply. In this respect, because the hair-treatment composition of this embodiment has high foaming properties, it is easily applied to hair that has been dyed with an oxidative hair dye. Improving the foaming properties of the hair-treatment composition by including a foaming aid in the hair-treatment composition is also conceivable, although this may lower the color fade suppressing effect on dyed hair by the hair-treatment composition.

Because the hair-treatment composition of this embodiment has high foaming properties, it can conform well to hair. This lowers the frictional resistance between hairs, making treatment of the hair by the hair-treatment composition smoother.

The lather created by foaming of the hair-treatment composition is fine, which also helps the hair-treatment composition to conform to the hair.

Following treatment with the hair-treatment composition, the hair has good finger combing properties. This appears to be due to the adsorption to the hair of the first and second amphoteric surfactants and the acidic amino acid contained in the hair-treatment composition.

The foregoing embodiment may be modified as follows.

The hair-treatment composition of the above embodiment is not limited to use on hair that has been dyed with an oxidative hair dye, and may be applied to hair that has been dyed with an acidic hair color (hair manicure). That is, to suppress color fade in hair dyed with an acidic hair color, the hair-treatment composition may be used in the post-treatment of the hair.

Hair to which the hair-treatment composition of the foregoing embodiment has been applied following dyeing of the hair with an oxidative hair dye may have the same hair-treatment composition repeatedly applied thereto daily or, for example, every 3 days, 5 days, or 7 days.

The hair-treatment composition of the above embodiment is not limited to single agent type compositions, and may instead be of a multiple agent type composed of a plurality of agents which are mixed together at the time of use.

Alternatively, the plurality of agents making up a multiple agent type hair-treatment composition may be mixed on the hair itself by successive application to the hair.

The oxidative hair dye used in the foregoing embodiment is not limited to a two-agent type composition of a first agent and a second agent. For example, at least one of the first agent and the second agent may itself be composed of a plurality of agents which are mixed together at the time of use.

EXAMPLES

The invention will be illustrated in more detail below by way of examples thereof and comparative examples.

The shampoos (hair-treatment compositions) of Examples 1 to 6 and Comparative Examples 1 to 4 formulated as shown in Tables 1 and 2 were prepared. In Tables 1 and 2, the numerical values indicating the contents of the respective ingredients in the shampoos are in units of percent by mass.

<Evaluation of Lathering, Lather Fineness, and Finger Combing Properties>

Twenty panelists who felt they had severe hair damage and dry skin shampooed their own hair using the respective shampoos in Examples 1 to 6 and Comparative Examples 1 to 4, and rated the lathering properties and lather fineness of each shampoo. After washing their hair with the shampoo in each of Examples and Comparative Examples, the panelists applied a test hair conditioner to the hair and subsequently rinsed with warm water, then dried the hair and rated the finger combing properties of the hair both immediately after drying and 6 hours after drying. The test hair conditioner used contained 3% by mass of cetanol, 2.5% by mass of cetrimonium chloride, 0.2% by mass of glyceryl monostearate, 1% by mass of glycerol, 0.2% by mass of methyl paraben, and 0.2% by mass of fragrance, with the balance being purified water.

The lathering properties of the respective shampoos in Examples 1 to 6 and Comparative Examples 1 to 4 were rated as follows. Cases in which 17 or more of the panelists responded that the shampoo had good lathering properties were given a rating of "5"; cases in which 13 to 16 of the panelists responded in this way were given a rating of "4"; cases in which 9 to 12 of the panelists responded in this way were given a rating of "3"; cases in which 5 to 8 of the panelists responded in this way were given a rating of "2"; and cases in which 4 or fewer of the panelists responded in this way were given a rating of "1."

The fineness of the lather for the respective shampoos in Examples 1 to 6 and Comparative Examples 1 to 4 were rated as follows. Cases in which 17 or more of the panelists responded that the lather was fine were given a rating of "5"; cases in which 13 to 16 of the panelists responded in this way were given a rating of "4"; cases in which 9 to 12 of the panelists responded in this way were given a rating of "3"; cases in which 5 to 8 of the panelists responded in this way were given a rating of "2"; and cases in which 4 or fewer of the panelists responded in this way were given a rating of "1."

The finger combing properties of the hair after using the respective shampoos in Examples 1 to 6 and Comparative Examples 1 to 4 were rated as follows. When a test hair conditioner was applied to the hair then rinsed off and the hair dried, cases in which 17 or more of the panelists responded that the hair had good finger combing properties both immediately after drying and 6 hours after drying were given a rating of "5"; cases in which 13 to 16 of the panelists responded in this way were given a rating of "4"; cases in which 9 to 12 of the panelists responded in this way were given a rating of "3"; cases in which 5 to 8 of the panelists responded in this way were given a rating of "2"; and cases in which 4 or fewer of the panelists responded in this way were given a rating of "1."

These evaluation results are shown in the "lathering," "lather fineness," and "finger combing" columns in Tables 1 and 2.

<Evaluation of Color Fade Suppressing Effect>
(1) Fabrication of Hair Bundle Samples for Testing Bundles of black hair having a length of about 20 cm were prepared, and each bundle was decolorized by a conventional method using a decolorizing agent (available from Hoyu Co., Ltd. under the trade name "Promaster EX LT"). Each bundle was then washed with a test shampoo. A 10% by mass of aqueous solution of sodium laureth sulfate was used as the test shampoo. Each bundle was then subjected to permanent waving treatment by a conventional method using a permanent waving preparation (available from Hoyu Co., Ltd. under the trade name "Lutea TG"), then was washed again using the above test shampoo and dried. After drying, each bundle was dyed brown using an oxidative hair dye (available from Hoyu Co., Ltd. under the trade name "Promaster EX B 7/6"), thereby giving hair bundle samples for testing.

(2) Application of the Shampoos of the Working Examples and Comparative Examples Hair bundle samples for testing that were in a wet state after being dyed with an oxidative hair dye were then washed using the respective shampoos of Examples 1 to 6 and Comparative Examples 1 to 4. The above test hair conditioner was applied to each of the hair bundle samples and subsequently rinsed off with warm water, following which the hair was dried with a hair dryer. Hair bundle samples for testing which were subjected a total of ten times to the series of steps consisting of washing using the respective shampoos, applying and rinsing off the test hair conditioner, then drying, and hair bundle samples for testing which were subjected to the same series of steps only once were both prepared.

(3) Evaluation

The color tone of hair bundle samples for testing which were subjected a total of ten times to the series of steps consisting of washing using the respective shampoos of Examples 1 to 6 and Comparative Examples 1 to 4, subsequently applying and rinsing off the test hair conditioner, then drying was compared by the 20 panelists with the color tone of hair bundle samples for testing which were subjected to the same series of steps only once. Cases in which 17 or more of the panelists responded that there was no observable difference between the color tones of both, i.e., that color fade was not observable even when repeated washing was carried out with the respective shampoos, were given a rating of "5"; cases in which 13 to 16 of the panelists responded in this way were given a rating of "4"; cases in which 9 to 12 of the panelists responded in this way were given a rating of "3"; cases in which 5 to 8 of the panelists responded in this way were given a rating of "2"; and cases in which 4 or fewer of the panelists responded in this way were given a rating of "1." These evaluation results are shown in the "color fade suppression" column in Tables 1 and 2.

TABLE 1

| | Examples | | | | | |
|---|---|---|---|---|---|---|
| | 1 | 2 | 3 | 4 | 5 | 6 |
| (A) $C_{12-14}$ Hydroxyalkyl hydroxyethyl sarcosine | 2 | 2 | 2 | 2 | 2 | 2 |
| (B) Lauryl dimethylaminoacetic acid betaine | 5 | — | — | — | 5 | 5 |
| (B) Cocamidopropylbetaine | — | 5 | — | — | — | — |
| (B) Sodium cocamphoacetate | — | — | 5 | — | — | — |
| (B) Sodium cocoamphopropionate | — | — | — | 5 | — | — |
| (C) Taurine | 0.3 | 0.3 | 0.3 | 0.3 | — | — |
| (C) L-Glutamic acid | — | — | — | — | 0.3 | — |
| (C) L-aspartic acid | — | — | — | — | — | 0.3 |
| TEA cocoyl glutamate | 7 | 7 | 7 | 7 | 7 | 7 |
| Polyoxyethylene cetyl stearyl diether | 0.5 | 0.5 | 0.5 | 0.5 | 0.5 | 0.5 |
| Polyglyceryl laurate-10 | 1 | 1 | 1 | 1 | 1 | 1 |
| (PEG/PPG/butylene/dimethicone) copolymer | 0.5 | 0.5 | 0.5 | 0.5 | 0.5 | 0.5 |
| Polyquaternium-10 | 0.4 | 0.4 | 0.4 | 0.4 | 0.4 | 0.4 |
| Dipropylene glycol | 5 | 5 | 5 | 5 | 5 | 5 |
| Ethanol | 2 | 2 | 2 | 2 | 2 | 2 |
| Glycerol | 2 | 2 | 2 | 2 | 2 | 2 |
| Hydrolyzed yeast extract | 0.0005 | 0.0005 | 0.0005 | 0.0005 | 0.0005 | 0.0005 |
| Sodium chloride | 1.5 | 1.5 | 1.5 | 1.5 | 1.5 | 1.5 |
| Disodium edetate | 0.05 | 0.05 | 0.05 | 0.05 | 0.05 | 0.05 |
| Etidronic acid | 0.2 | 0.2 | 0.2 | 0.2 | 0.2 | 0.2 |
| Sodium benzoate | 0.3 | 0.3 | 0.3 | 0.3 | 0.3 | 0.3 |
| Methyl paraben | 0.2 | 0.2 | 0.2 | 0.2 | 0.2 | 0.2 |
| Fragrance | 0.5 | 0.5 | 0.5 | 0.5 | 0.5 | 0.5 |

TABLE 1-continued

|  |  | Examples | | | | | |
|---|---|---|---|---|---|---|---|
|  |  | 1 | 2 | 3 | 4 | 5 | 6 |
| Purified water | | balance | balance | balance | balance | balance | balance |
| Total | | 100 | 100 | 100 | 100 | 100 | 100 |
| Evaluation | Lathering | 5 | 5 | 5 | 5 | 5 | 5 |
| | Lather fineness | 5 | 5 | 5 | 5 | 5 | 5 |
| | Finger combing | 5 | 5 | 5 | 5 | 5 | 5 |
| | Color fade suppression | 5 | 5 | 5 | 5 | 5 | 5 |

TABLE 2

|  |  | Comparative Examples | | | |
|---|---|---|---|---|---|
|  |  | 1 | 2 | 3 | 4 |
| (A) | $C_{12-14}$ Hydroxyalkyl hydroxyethyl sarcosine | — | 7 | 2 | 2 |
| (B) | Lauryl dimethylaminoacetic acid betaine | 7 | — | 5 | 5 |
| (C) | Taurine | 0.3 | 0.3 | — | — |
| | Glycine | — | — | — | 0.3 |
| TEA cocoyl glutamate | | 7 | 7 | 7 | 7 |
| Polyoxyethylene cetyl stearyl diether | | 0.5 | 0.5 | 0.5 | 0.5 |
| Polyglyceryl laurate-10 | | 1 | 1 | 1 | 1 |
| (PEG/PPG/butylene/dimethicone) copolymer | | 0.5 | 0.5 | 0.5 | 0.5 |
| Polyquaternium-10 | | 0.4 | 0.4 | 0.4 | 0.4 |
| Dipropylene glycol | | 5 | 5 | 5 | 5 |
| Ethanol | | 2 | 2 | 2 | 2 |
| Glycerol | | 2 | 2 | 2 | 2 |
| Hydrolyzed yeast extract | | 0.0005 | 0.0005 | 0.0005 | 0.0005 |
| Sodium chloride | | 1.5 | 1.5 | 1.5 | 1.5 |
| Disodium edetate | | 0.05 | 0.05 | 0.05 | 0.05 |
| Etidronic acid | | 0.2 | 0.2 | 0.2 | 0.2 |
| Sodium benzoate | | 0.3 | 0.3 | 0.3 | 0.3 |
| Methyl paratoen | | 0.2 | 0.2 | 0.2 | 0.2 |
| Fragrance | | 0.5 | 0.5 | 0.5 | 0.5 |
| Purified water | | balance | balance | balance | balance |
| Total | | 100 | 100 | 100 | 100 |
| Evaluation | Lathering | 3 | 1 | 2 | 2 |
| | Lather fineness | 2 | 2 | 2 | 2 |
| | Finger combing | 3 | 2 | 2 | 3 |
| | Color fade suppression | 1 | 5 | 3 | 3 |

As shown in Tables 1 and 2, in the shampoos of Examples 1 to 6, not only the ratings for lathering (i.e., foaming properties) and color fade suppression, but also the ratings for lather fineness and finger combing were all good.

By contrast, in the shampoo of Comparative Example 1, which did not contain the first amphoteric surfactant, the rating for color fade suppression in particular was inferior to those of the shampoos in the examples according to the invention.

In the shampoo of Comparative Example 2, which did not contain the second amphoteric surfactant, the rating for lathering was inferior to those of the shampoos in the examples according to the invention.

In the shampoo of Comparative Example 3, which did not contain an acidic amino acid, and in the shampoo of Comparative Example 4, which contained the neutral amino acid glycine instead of an acidic amino acid, the ratings for lathering and color fade suppression were inferior to those of the shampoos in the examples according to the invention. It was apparent from these results that using an acidic amino acid is essential for improving the ratings for lathering and color fade suppression.

The invention claimed is:

1. A hair-treatment composition comprising:

(A) a first amphoteric surfactant having a structure represented by the following general formula (1)

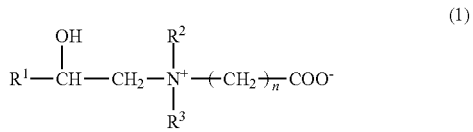

(where R1 represents an alkyl group the carbon number of which is 6 to 20; R2 represents a methyl group, an ethyl group, or a hydroxyethyl group; R3 represents a methyl group, an ethyl group, or a —CH$_2$COOH group; and n is an integer from 1 to 3);

(B) at least one type of second amphoteric surfactant selected from the group consisting of fatty acid amide propyldimethylaminoacetic acid betaines, alkyldimethylaminoacetic acid betaines, N-acylaminoethyl-N-2-hydroxyethylaminocarboxylic acid salts, and N-acylaminoethyl-N-carboxymethoxyethylaminocarboxylic acid salts; and (C) an acidic amino acid.

2. The hair-treatment composition according to claim 1, wherein the acidic amino acid is of at least one type selected from the group consisting of L-glutamic acid, L-aspartic acid, and taurine.

3. The hair-treatment composition according to claim 1, wherein the second amphoteric surfactant is of at least one type selected from the group consisting of cocamidopropyl betaine, lauryldimethylaminoacetic acid betaine, sodium cocoamphoacetate, sodium cocoamphopropionate, sodium cocoamphodiacetate, and sodium cocoamphodipropionate.

4. The hair-treatment composition according to claim 1, wherein the composition is adapted for use in a post-treatment for hair dyed with an oxidative hair dye.

5. A hair-treatment method comprising applying the hair-treatment composition according to claim 1 to hair in a wet state immediately after the hair is dyed with an oxidative hair dye.

6. The hair-treatment method according to claim 5, further comprising, following application of the hair-treatment composition to hair:

washing and drying the hair; and applying the same hair-treatment composition again to the washed and dried hair.

* * * * *